United States Patent [19]

Kleinmann

[11] 4,314,966

[45] Feb. 9, 1982

[54] METHOD OF CONTROL OF ACID DRAINAGE FROM EXPOSED PYRITIC MATERIALS

[76] Inventor: Robert Kleinmann, 5774 Smith Dr., Bethel Park, Pa. 15102

[21] Appl. No.: 186,898

[22] Filed: Sep. 12, 1980

Related U.S. Application Data

[63] Continuation-in-part of Ser. No. 94,426, Nov. 15, 1979, abandoned.

[51] Int. Cl.³ .............................................. A61L 2/22
[52] U.S. Cl. ...................................... 422/28; 424/19; 424/22; 424/30; 422/32; 422/900
[58] Field of Search ............... 424/19, 22, 30; 422/28, 422/32, 900

[56] References Cited

U.S. PATENT DOCUMENTS

| | | | |
|---|---|---|---|
| 3,094,846 | 6/1963 | Peeler | 422/1 |
| 3,306,728 | 2/1967 | Campbell | 71/64 F |
| 3,400,011 | 9/1968 | Fox | 71/64 F |
| 3,443,882 | 5/1969 | Flynn | 422/900 |
| 3,590,119 | 6/1971 | Cardarelli | 424/78 |
| 3,639,583 | 2/1972 | Cardarelli | 424/125 |
| 3,740,419 | 6/1973 | Campbell | 424/38 |
| 3,851,053 | 11/1974 | Cardarelli | 424/78 |
| 3,928,564 | 12/1975 | Cardarelli | 424/78 |
| 4,012,221 | 3/1977 | Walker | 424/22 |
| 4,166,111 | 8/1979 | Cardarelli | 424/78 |

OTHER PUBLICATIONS

Dugan, P. et al.: "Acid Production by Ferrobacillus Ferrooxidans and its Relation to Water Pollution", *Developments in Industrial Microbiology*, vol. 5, 1964, pp. 250-257.

*Primary Examiner*—Dennis L. Albrecht

[57] ABSTRACT

Acid drainage from exposed pyritic material such as coal mine tailings is reduced through the controlled application of anionic detergents which inhibit the bacterium *Thiobacillus ferrooxidans*. The controlled application of anionic detergent comprises an initial application of anionic detergent in sufficient quantities to satisfy the adsorptive capacity of clay or clay-sized particles overlying the pyritic material coupled with the application of an anionic detergent inhibitor of *Thiobacillus ferrooxidans* from a slow release matrix containing the inhibitor. The two applications are to intercept infiltrating water up-gradient of the pyritic material or strata. The amount of matrix employed is calculated in accordance with a described formula. The method can be used to reduce acidity in drainage from pyritic mine tailings, coal mines, coal refuse piles and construction sites at which acid drainage is a problem.

Acid drainage is also reduced by the mere controlled application of specific anionic detergents which inhibit the bacterium *Thiobacillus ferrooxidans* utilizing a detergent-containing matrix which provides detergent concentrations of greater than 10 ppm and preferably greater than 25 ppm in the infiltrating water.

17 Claims, 1 Drawing Figure

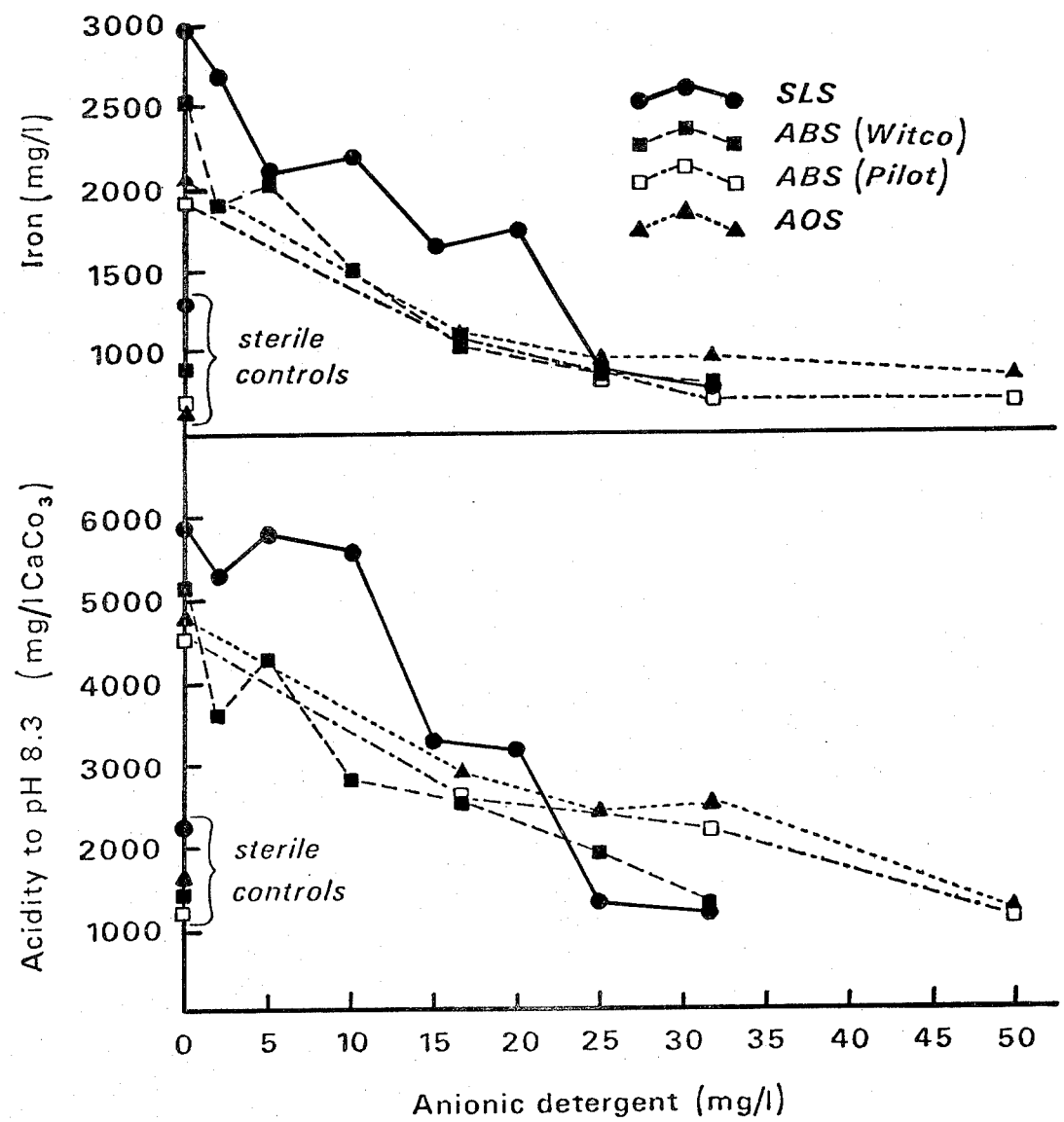

METHOD OF CONTROL OF ACID DRAINAGE FROM EXPOSED PYRITIC MATERIALS

RELATED APPLICATION

This application is a Continuation-in-Part of my copending application, Ser. No. 94,426, filed Nov. 15, 1979, abandoned on the filing date of this application, all the teachings of which copending application are incorporated herein by specific reference thereto.

BACKGROUND OF THE INVENTION

1. Field of the Invention

This invention relates to a method for the reduction of acidity in drainage from pyritic mine tailings, coal mines, coal refuse piles and construction sites.

2. Description of the Prior Art

Acid drainage results from the oxidation of iron pyrite ($FeS_2$) associated with coal, mine tailings and overburden material. The problem of acid formation also may occur during building or road construction due to pyrite present in the disturbed strata. The conventional technique to overcome this problem has been to collect the drainage from the area and then neutralize it with lime and/or limestone.

Previous research by biologists suggests that a bacterium, *Thiobacillus ferrooxidans*, plays a role in the acid formation process. However, geologists have remained sceptical of such research primarily because the laboratory experimental conditions tend to deviate radically from actual field conditions. Hence any correlation between laboratory and field conditions is suspect.

The tolerance of *T. ferrooxidans* to a large range of chemical substances has been examined in the literature. Indeed, two detergents, alkyl benzene sulfonate and sodium lauryl sulfate, were tested by Dugan and Lundgren in 1964 and shown to inhibit *T. ferrooxidans* at concentrations of 2-5 ppm in culture media. Another detergent was also tested and found inhibitory at only extremely high concentrations. The inhibition observed was attributed by Dugan and Lundgren to a coating of the bacteria caused by the detergents' alkyl side chain.

It is of course possible to protect coal from contact with water and thereby prevent formation of acid drainage by coating each individual particle with various oils and waxes. Moreover, coal may be protected as disclosed in U.S. Pat. No. 2,204,781, Wattles, by spraying the outside surface of piles or large masses of coal with a material congealable at atmospheric temperatures whereby a non-tacky weather resistant jacket adherent to the coal at the surface of the pile or mass is formed. However, both of the foregoing procedures require substantial expenditures of coating material, and are not practical where the primary purpose is to avoid acid drainage as opposed to the prevention of water contact.

One prior art approach to prevention of acid drainage relates to treatment with an aqueous alkali metal silicate solution which reacts with acid present to form a sila gel which in turn may coat the pyrite surface. (U.S. Pat. No. 3,094,846). Another prior art method of preventing acid drainage involves use of a mixture of pulverized phosphate and sulfuric acid to precipitate soluble iron as phosphates which in turn may coat the pyrite surface, (U.S. Pat. No. 3,443,882).

In accordance with this invention acid drainage in a pyritic material which is exposed to water is controlled by addition of at least about 10 ppm of an anionic detergent capable of inhibiting *T. ferrooxidans* to the water which contacts the exposed material. The concentration is necessarily higher than that previously reported to be required to inhibit *T. ferrooxidans* in culture media. In order to avoid repopulation, the addition is effected by controlled release from a matrix containing anionic detergent dispersed therein. Controlled addition is accomplished by placement of the matrix to intercept infiltrating water upgradient of the pyritic material. The quantity of anionic-detergent containing matrix required to effect the controlled release is calculated in accordance with the formula set forth in the summary of the invention.

I have developed a method of dealing with acid drainage which, unlike the conventional prior art, does not address the problem by treating the resultant acid, but rather prevents acid formation in a facile and economically viable manner.

SUMMARY OF THE INVENTION

This invention relates to reducing acid drainage in a pyritic material which is exposed to water by controlled addition of at least about 10 ppm of an anionic detergent capable of inhibiting *T. ferrooxidans* to the water which contacts the exposed material by controlled release from a matrix containing anionic detergent dispersed therein. The matrix may be an elastomer and may be comprised of rubber. The matrix may alternatively be a high melting point wax. Controlled addition is accomplished by placement of the matrix to intercept infiltrating water up-gradient of the pyritic material.

The pyritic material which may be treated includes pyritic mine tailings, pyritic coal mines, pyritic coal refuse piles and pyritic construction sites; however, any mass of pyritic material susceptible to acid drainage may be treated in accordance with this invention.

The anionic detergent may be selected from the group consisting of *Thiobacillus ferrooxidans*-inhibiting water soluble salts of (a) alkyl aryl sulfonic acids, (b) alkyl sulfonic acids, (c) alkenyl sulfonic acids, (d) sulfonated alkyls, (e) sulfonated alkenyls, (f) sulfated monoglycerides, (g) sulfated fatter esters. Above a pH of about 2.5, sodium lauryl sulfate is preferable.

This invention relates to a method of reducing acid drainage in a pyritic material which is exposed to water, which method comprises adding at least about 10 mg of an anionic detergent which inhibits the bacterium, *Thiobacillus ferrooxidans* per liter of said water which contacts the exposed material.

Pyritic material at construction sites is predominately associated with clays or shales. Pyritic material is also associated with shale tailings obtained after extraction of hydrocarbonaceous material therefrom. Moreover, coal refuse piles contain substantial quantities of clay and shale fragments. Accordingly the overall treatment to reduce acid drainage should preferably be adapted to provide for saturating adsorption sites or these non-pyritic particles associated with pyritic materials during the initial stage of anionic detergent application. Initial application of anionic detergent to saturate adsorptive sites of adsorbtive compositions associated with the pyritic material can be before, at the time of or after placement of the controlled release matrix. Such initial treatment may precede or follow placement of the matrix by a matter of weeks, although substantially longer periods are also suitable.

The most-preferred embodiment of this invention comprises an initial application of anionic detergent to saturate the adsorptive capacity of clay particles associated with the pyritic material coupled with addition of anionic detergent by controlled release from a matrix containing said anionic detergent dispersed therein. Specifically, the initial application consists of an anionic detergent applied at concentrations greater than 50 mg per liter of water and typically at least 100 mg per liter of water. Controlled release addition of anionic detergent is effected by controlled release from a matrix containing said anionic detergent dispersed therein. Specifically the addition is effected by placing the matrix containing said anionic detergent dispersed therein to intercept infiltrating water up-gradient of the pyritic material.

The quantity of matrix required to effect controlled release which is placed up-gradient of the pyritic material is represented by Q, determined in accordance with the following formula:

$$Q = \frac{Pa\ I\ A\ C}{Dr\ R} \times 10$$

Q = the quantity of detergent-continuing matrix in kg
Pa = the numeral representing the annual average precipitation in area [m]
I = percent infiltration
A = the numeral representing the area to be treated in $M^2$
Dr = the numeral representing the detergent-release rate for matrix at particle size range to be used, mg detergent/kg matrix year
R = the numeral representing the effective release-life of the matrix in years
C = the numeral representing the optimal average concentration of detergent in mg/l The percent infiltration, I, is site-specific and generally is estimated at 50% for reclaimed or undisturbed land surfaces and 75% for coal refuse and unreclaimed surface mines.

The annual detergent release rate, Dr, is determined by measuring detergent release under saturated conditions. It is expressed as mg detergent/kg matrix year.

The effective release life of the matrix is dependent on the specific matrix and falls within the range of about 2 to about 5 years.

The optimal average concentration of detergent is generally about 20 to about 25 mg/l for sodium lauryl sulfate and about 20 to about 40 mg/l for the other anionic detergents.

Preferably, the anionic detergent is added in an amount of at least about 25 mg per liter of said water. The matrix is preferably in particulate form with shredded particles of a size of about one inch preferred. Anionic detergents suitable for this invention are (a) alkyl aryl sulfonic acids, (b) alkyl sulfonic acids, (c) alkenyl sulfonic acids, (d) sulfonated alkyls, (e) sulfonated alkenyls, (f) sulfated monoglycerides and (g) sulfated fatty esters. Among the foregoing anionic detergents are the long chain alpha olefin sulfonates; soluble salts of alkenyl sulfonic acid such as the sodium salt of $C_{14}-C_{16}$ alpha olefin sulfonates; water soluble alkenyl aryl sulfonic acid salts; water soluble alkyl aryl sulfonic acid salts such as sodium alkylnaphthalene sulfonate and sodium alkyl benzene sulfonate; water soluble salts of sodium lauryl sulfate; and water soluble salts of sulfated monoglyceride.

The matrix may be an elastomer such as rubber or a high melting point wax or other suitable material capable of slow release of the detergent.

DETAILED DESCRIPTION OF THE INVENTION

One aspect of this invention resides in the discovery that high levels of certain anionic detergents having a long alkyl chain of 6 or more carbon atoms, are effective in reducing or stopping acid drainage from water-exposed pyritic materials. Concentrations of at least about 10 ppm and preferably within the range of from about 10 ppm to about 20 ppm have been found to inhibit bacterial activity of *T. ferrooxidans*, and levels above about 20 ppm kill the bacteria.

An important aspect of this invention relates to the initial application of anionic detergent. The primary purpose of this initial application is to reduce subsequent adsorption of anionic detergent by clay particles up-gradient of the pyritic material by saturating absorptive capacity which would otherwise reduce the effectiveness of the controlled release. A secondary purpose is a rapid reduction in population of *Thiobacillus ferrooxidans* in and up-gradient of the pyritic material.

The amount of anionic detergent required for the initial application depends on the volume of pyritic material, the volume of overlying material and the percent clay content of the overlying material. Preferably, the detergent is applied in a concentration of at least 100 mg/l, in sufficient volume so that each acre-foot of pyritic material is treated with the equivalent of 7 pounds of detergent (ie. 85 gallons of 1% solution, or 1,000 gallons of 850 ppm solution). In practice, the initial application can be estimated in one of two ways:

1. by estimating adsorption from the percent clay and slit present in overlying material. Each foot of slit-clay can be assumed to adsorb approximately 10–15% of the initial application. Strata containing lesser amounts of slit and clay can be assumed to adsorb proportionally lower amounts. Thus, for example, if there was six feet of disturbed strata overlying the pyritic material, of which four feet was primarily fine-grained and two feet was a mixture of fine- and coarse-grained material, an initial application would be calculated by multiplying the required concentration in the pyritic material by the mount adsorbed by the overburden, ie. four feet of fine-grained material will adsorb 40–60%, two feet of mixed material will adsorb 10–15%. Thus a minimum application for the given strata would be approximately three times that required to treat the pyritic material. Thus, for a quarter-acre site containing a foot of potentially acid-forming material and the described overburden, an appropriate initial application estimate would be 5 pounds of detergent (7 pounds of detergent×0.25 acre-feet×3) or 1,000 gallons of 600 ppm solution.

2. by application of detergent at concentrations of at least 100 ppm until groundwater samples, taken immediately down-gradient at the pyritic material, foam upon gentle agitation. Monitoring stations should be as near as possible to the pyritic material; it is not desirable nor appropriate to apply detergent until streams in the area are foaming.

Another aspect of this invention resides in the discovery that the potential problem associated with the high solubility of anionic detergents and easy re-establishment of bacteria where anionic detergent is not continuously present, can be overcome by the continuous and controlled release of anionic detergent from a matrix.

Where an elastomeric matrix, e.g. a rubber comprising matrix is employed, preferably the ratio by weight of anionic detergent to elastomer is from about 30 to about 80 parts by weight of anionic detergent per hundred parts by weight matrix.

Examples of suitable controlled release compositions are set forth in the table which follows:

| FORMULATIONS CONTROLLED RELEASE ANIONIC SURFACTANT (DIFFUSION - DISSOLUTION) | |
|---|---|
| I | |
| natural rubber | 50 parts |
| thermoplastic styrene butadiene | 50 parts |
| carbon black | 10 parts |
| anionic detergent | 10–50 parts |
| II | III |

Still another aspect of my invention resides in my discovery that water soluble alkenyl sulfonates such as alpha olefin sulfonates, and specifically long chain alpha olefin sulfonates, suitably $C_{14}$–$C_{16}$ admixtures are effective as *Thiobacillus ferrooxidans* inhibitors when dispersed within a slow release matrix. Sodium salts of $C_{14}$–$C_{16}$ alpha olefin sulfonates are particularly preferred.

I have also discovered that water soluble alkylnaphthalene sulfonates such as "Alkanol" XC, a sodium alkylnaphthalene sulfonate produced by the DuPont Company are very effective as *Thiobacillus ferrooxidans* inhibitors when dispersed within a slow release matrix.

In addition to the foregoing I have further discovered that water soluble sulfated monogylerides operate in the same manner as the foregoing alkenyl sulfonates and alkylnaphthalene sulfonates.

It is important to add that, although certain groups of anionic detergents have been found to be effective in reducing the acidity of pyritic mine tailings, anionic surfactants such as "Zonyl" fluorosurfactants, sulfated alkyl ethers, and sulfated ethoxylated alkyl phenols are ineffective in the environment associated with mining drainage, the water soluble salts previously related have been found to be effective. Among the suitable anionic detergents are alkyl aryl sulfonates, long chain alcohol sulfates, olefin sulfates and sulfonates, sulfated monoglycerides, sulfated ethers, sulfo-succinates and alkane sulfonates.

The configuration of matrix which has been found most suitable for use in connection with the method of this invention is particulate, of a size generally of about one inch±one half inch with shredded material being most preferred. Such particles because of irregular surface best retain the configuration of the matrix mass and offer maximal surface area.

EXAMPLE

This example illustrates the results of laboratory testing of pyritic overburden materials under simulated field conditions developed for the purpose of laboratory testing.

Sodium lauryl sulfate (SLS), the sodium and calcium salts of linear alkylbenzene sulfonate (ABS) and alpha olefin sulfonate (AOS) were tested as inhibitors. Natural and synthetic rubber formulations and the amide ester of monoethanolamine and stearic acid (a high melting point wax) were tested as release agents.

Pyritic Material Tested

For laboratory testing coal and overburden materials, collected from Clarion, Pa. and averaging 5% total sulfur, were crushed and sieved to a size within the range of from 0.2 to 2.0 cm. The particles were rinsed with deionized, distilled water.

*T. ferrooxidans* Employed

*T. ferrooxidans* obtained from the American Type Culture Collection (ATCC #13728), was cultured in 9-K medium.

Composition of Simulated Rainfall

Simulated rainfall infiltration consisted of a synthetic ground water formulation of water containing 50 ppm $CaCO_3$; 25 ppm $M_gSO_4$; 2 ppm $(NH_4)_2$ and 0.25 ppm $KH_2PO_4$.

Apparatus and Procedure

Tubulated desiccators were used to simulate the humid environment of the intermediate belt of the zone of aeration. The experiments were performed in perforated polypropylene beakers, each containing 50 g rinsed crushed sample material. The beakers were positioned so as to drain into slightly larger beakers and the entire double beaker assemblage was autoclaved before being placed on a tray inside the desiccator. Water beneath the tray was heated for about 15 minutes to provide a humid atmosphere. Two 0.5 cm diameter tubes were inserted through the desiccator lid to allow controlled contact with the atmosphere and to simulate rainfall infiltration. To simulate the presence of *T. ferrooxidans* in natural mine infiltration, a 0.1 ml inoculum of the 9-K medium was trickled onto the samples every three days. Immediately following this, 6.0 ml of synthetic groundwater, with varying concentrations of detergent, was applied. Sterile controls received no inoculum.

At the end of each run, the contents of the beakers were filtered and rinsed with 100 ml deionized, distilled water. Approximately 0.5 g of the test material was placed in 9-K culture medium to test for *T. ferrooxidans*. Oxidation of the medium in 3–4 days showed that the bacterium was present and uninhibited. Oxidation which occurred after 6–10 days was interpreted as lowered population density, due to either partial inhibition or bacteriostatic action.

The collected filtrate was analyzed for total dissolved iron by atomic absorption spectrophotometry, and for acidity, by the hot peroxide method (Standard Methods, No. 402 of "Standard Methods for the Examination of Water and Wastewater", 14th ed., A.P.H.A. Washington, D.C. 1976.)

Inhibitory Effects of Anionic Detergents

Referring to FIG. 1, the effect of sodium lauryl sulfate (LSL); linear alkyl benzenesulfonate (ABS), from Witco C-18, 90% active content; linear alkenyl benzene sulfonate (ABS) from Pilot, $C_{18}$, also 90% active content, and alpha olefin sulfonate (AOS) $C_{14}$–$C_{16}$, 88% active content, in reducing acidity and iron concentrations in water contacting pyritic coal particles containing 5% sulfur is shown.

The inhibitory effect was especially marked for sodium lauryl sulfate, which was also the most effective in limiting bacterial population. Samples containing SLS at concentrations increasing from 5 to 20 ppm showed proportionally delayed growth when transferred to 9-K culture medium. At 25 ppm, SLS was bactericidal, reducing acidity and iron concentrations to about that of sterile controls. The other anionic detergents as will be noted by reference to FIG. 1 required somewhat higher concentrations to obtain the same effects.

The concentration of detergent necessary to inhibit *T. ferrooxidans* in the simulated mine environment was determined to be greater than that required in 9-K culture media. It is possible that the substrate material reduces the vulnerability of the bacteria, that the detergent does not saturate all of the crushed material before draining or that the effectiveness of detergents in synthetic groundwater differs from that in 9-K medium.

TABLE 1

Release of sodium lauryl sulfate from wax (particle size 4-8 mm) under saturated conditions.

| Detergent concentration in wax (weight percent) | Length of experiment (days) | Avg. release per g of material ($\mu$g/day) |
| --- | --- | --- |
| 9 | 1 | 70 |
| 21 | 1 | 120 |
| 33 | 1 | 75 |
| 9 | 30 | 9 |
| 21 | 30 | 8 |
| 33 | 30 | 12 |

TABLE 2

| Composition | Detergent composition in rubber | Particle size (mm) | Avg. release per g of material ($\mu$g/day) at pH 4.5 |
| --- | --- | --- | --- |
| vulcanized natural rubber | 14.5% SLS | 8-40 | 4 |
| | 14.5% Na-AB | 8-40 | 4 |
| | 20% Ca-ABS | 8-40 | 6 |
| | 20% SLS | 8-40 | 10 |
| | 20% Na-ABS | 8-40 | 12 |
| | 26% Ca-ABS | 8-40 | 12 |
| | 26% SLS | 8-40 | 30 |
| | 31% SLS | 8-40 | 40 |
| | 37% SLS | 8-40 | 45 |
| | 41% SLS | 8-40 | 40 |
| unvulcanized; thermoplastic SBR + natural rubber | 27% SLS | 8-40 | $20^a$–$50^b$ |
| | 27% SLS | 4-8 | $120^a$–$150^b$ |
| | 27% SLS | .42-4. | $185^c$ |
| sponge rubber | 13% SLS | 4-8 | 14 |

[a] release rates at pH 2.5
[b] release rates at pH 4.5
[c] release rates at pH 2.5 and 4.5 were equal

Inhibitory Effect of Controlled Release of Anionic Detergents in Simulated Field Conditions Controlled release was investigated in laboratory simulated field conditions as a means of administering anionic detergents with each rainfall over prolonged period to a pyritic coal pile wherein the coal contained 5% sulfur. The rubber-detergent formulations were prepared in a Brabender plasticorder by premixing the non-curing ingredients and adding them with the rubber, followed by the curing ingredients after a minute and a half. The wax matrices were prepared by mixing the detergent into the melted wax with a magnetic stirrer and hot plate. All release materials were rinsed before testing.

The rate of release from 5.0 g each of the below-described wax and rubber formulations was ascertained by measuring detergent concentration when the material was rinsed each week, and alternatively, when it was continuously submerged in distilled, deionized water, adjusted to pH 4.5, and in some cases pH 2.5, with $H_2SO_4$. Also examined was the effect of particle size on detergent release, using duplicate runs of sieved size fractions of 0.42-4 mm, 4-8 mm and 8-40 mm. In all cases, detergent concentration was determined by the methylene blue method. "Standard Methods for the Examination of Water and Wastewater", 14th ed., A.P.-H.A., Washington, D.C. 1976.

The results of anionic detergent release from wax and rubber matrices is indicated below in Tables 1 and 2 respectively.

As will be noted by reference to Table 1, release of the detergents from the wax formulations was initially fast, but decreased rapidly with time. However, formulations containing 33% detergent showed a second rapid-release period after about two months as porosity caused by detergent dissolution led eventually to complete disaggregation. Accordingly, high molecular weight formulations which are formulated for long term utilization should comprise at least about ⅓ anionic detergent.

The diffusion-dissolution of detergent from rubber matrix proceeds at a release rate proportional to the square root of time, until approximately 60% of the active agent has been released, after which the release rate drops off exponentially. Thus, the ideal release rate for a rubber matrix would be one in which 60% depletion coincides approximately with the stability lifespan of the matrix.

The daily average release rate for the vulcanized natural rubber formulations set forth in Table 2 would require in excess of twelve years for 60% release of anionic agent release before breakdown of the rubber. Assuming as the lifespan of the rubber 2-5 years, in order to obtain an ideal coincidence of depletion and matrix lifespan, the mixture of 50 parts natural rubber to 50 parts thermoplastic styrene butadiene rubber, which can be handled without vulcanization, best approximated the ideal formulation. An average release rate of 50 mg/day per g of matrix was observed in the foregoing formulations

Inhibitory Effect of Controlled Release of Anionic Detergent Under Field Conditions The detergent-matrix combination which optimized rate of release and inhibition of *T. ferrooxidans* comprising a matrix of an unvulcanized admixture of SBR and rubber was applied to one of two 25 ton coal refuse piles in central Pennsylvania made available by Barnes and Tucker Coal Co. Each pile sat on a plastic sheet and was graded so as to drain in one direction. A perforated pipe ran through each pile and drained into a collecting bucket, which was emptied after sampling. Seven slabs of unvulcanized admixture, each approximately 0.3 m$^2$ in areas and totalling 27 kg (of which about 27% was an anionic detergent, sodium lauryl sulfate), were placed beneath the surface of one of the piles in such a manner as to minimize interference with natural infiltration. Samples of the drainage from each pile were analyzed for acidity, total dissolved iron, ferrous iron, detergent concentration and population of *T. ferrooxidans* by most probable number. ("Standard Methods for the Examination of Water and Wastewater", 14th ed., A.P.H.A., Washington, D.C. 1976.)

The amount of anionic detergent containing matrix necessary for the coal refuse pile was determined from the average laboratory release rate, the horizontal area of the pile (16 m$^2$) and the average annual rainfall for the area (approximately 100 cm), as heretofor more fully explained. The actual concentration of dissolved detergent dependant on the time interval between rainstorms and the quantity of rainfall and is, therefore, not precisely calculable. It is generally necessary that detergent concentration exceed 10 ppm, preferably 15 ppm and occasionally 25 ppm to prevent bacterial repopulation; therefore, it is preferable to exceed rather than fail to reach the minimal detergent concentration required.

After about 100 days acidity and iron values for the treated pile were less than 1/80 times those observed in the drainage from the control pile. However, detergent concentration was lower than anticipated (approximately 10 ppm) due to the low surface area of the rubber, causing a second rise in acidity, which eventually resulted in acidity $\frac{1}{3}$ the level of the control pile.

The same detergent-rubber combination was field tested on acid-producing overburden material using a pair of leaching tubs at a site in northern West Virginia. The tubs were buried to ground level in pyritic shale and enclosed approximately 0.3 m$^2$ of the material. One tub was treated with approximately 1.5 kg of the unvulcanized SLS-rubber in pieces approximately 30 cm$^2$ in area; the other was left untreated as a control. Drainage was collected via tubing leading from the bottom of each, and was analyzed for acidity, total dissolved iron, ferrous iron, detergent concentration and presence or absence of *T. ferrooxidans*.

The West Virginia field test tested the effect of controlled release of anionic detergent on acid production in an abandoned surface mine. Abandoned coal mines produce over three-fourths of the acid drainage of Appalachia. Sufficient rubber was applied to generate an anticipated detergent concentration of at least 25 ppm, assuming a release rate under acid conditions of 20 mg/day per g of matrix. Two weeks after application of the rubber, approximately 250 milliliters of 30% detergent solution was mixed with 1,000 milliliters of water and added to the section treated with the detergent releasing rubber matrix. This application was adopted to saturate the adsorptive sites which were present in the oberburden clays associated with the residual pyritic materials of the abandoned surface mine area where the rubber matrix was applied. The rubber was added to the more acid-producing section and generated a detergent concentration which ranged from 10 to 60 ppm in the drainage (the latter after the winter freeze). *T. ferrooxidans* was observed in the drainage from the untreated control throughout the duration of the experiment. However, it was only present in drainage for three weeks after treatment with the controlled release material and the aqueous diluted detergent solution.

Acidity before treatment averaged approximately 30,000 mg/l (as CaCO$_3$) with a pH of 2.1. Two months after treatment, significant decrease in acidity was observed with 95% reduction after six months. Nine months after treatment, pH of the drainage from the treated section was 6.86 with only 25 mg/l acidity as compared to pH in the control section of 2.0 and acidity of 28,250 mg/l.

It should be pointed out that the effect of particle size on the rate of detergent release has been discovered to be a viable method of obtaining optimal release rate. Table 2 includes release rates for unvulcanized rubber of various size ranges, the finest-grained of which was a coarse powder (between sieve sizes 5 and 40) that gave an average release of 185 mg/day per g of rubber. This would give an expected release life of 2.5 years before 60% depletion, which is a reasonable estimate of the stable lifespan of the buried rubber. At this rate, again assuming an average annual rainfall of 100 cm and a desired detergent concentration of 25 ppm, 37 kilograms would treat a hectare of coal refuse at a cost of $50–75 ($20–30/acre) per year.

It will be obvious that modifications to this process may be made and it is intended to cover such modifications and changes as would occur to one skilled in the art, as the following claims permit and consistent with the prior art.

What I claim is:

1. A method of reducing acid drainage in a pyritic material which is exposed to water, which method comprises:
    (1) treating each acre-foot of pyritic material with at least seven pounds of a first anionic detergent which inhibits the bacterium *Thiobacillus ferrooxidans;* and
    (2) adding at least 10 mg of a second anionic detergent which inhibits the bacterium *Thiobacillus ferrooxidans* per liter of said water which contacts the exposed material, said addition being effected by controlled release from a matrix containing said second anionic detergent dispersed therein; said first and second anionic detergent being selected from the group consisting of *Thiobacillus ferrooxidans*-inhibiting water soluble salts of (a) alkyl aryl sulfonic acids, (b) alkyl sulfonic acids, (c) alkenyl sulfonic acids, (d) sulfated fatty esters.

2. The method of claim 1 wherein the first and second anionic agents are the same.

3. The method of claim 1 wherein said addition is effected by placing the matrix containing said second anionic detergent dispersed therein to intercept infiltrating water up-gradient of the pyritic material.

4. The method of claim 3 wherein the quantity of matrix placed up-gradient of the pyritic material is represented by Q, determined in accordance with the following formula:

$$Q = \frac{Pa\,I\,A\,C}{Dr\,R} \times 10$$

Where:

A = the quantity of detergent-continuing matrix in kg
Pa = the numeral representing the annual average precipitation in area in m
I = percent infiltration
A = the numeral representing the area to be treated in m²
Dr = the numeral representing the detergent-release rate for matrix at particle size range to be used, mg detergent/kg matrix year
R = the numeral representing the effective release-life of the matrix in years
C = the numeral representing the optimal average concentration of detergent in mg/l.

5. The method of claims 1 or 3 wherein the anionic detergent is added in an amount of at least about 25 mg per liter of said water.

6. The method of claim 4 wherein said matrix is in particulate form.

7. The method of claim 6 wherein said particles are shredded particles.

8. The method of claim 4 wherein the anionic detergent is a long chain alpha olefin sulfonate.

9. The method of claim 4 wherein the water-soluble salt of alkenyl sulfonic acid is a sodium salt of $C_{14}$-$C_{16}$ alpha olefin sulfonates.

10. The method of claim 4 wherein the anionic detergent is a water soluble alkyl aryl sulfonic acid salt.

11. The method of claim 4 wherein the water soluble alkyl aryl sulfonic acid salt is a sodium alkylnaphthalene sulfonate.

12. The method of claim 4 wherein the water soluble alkyl aryl sulfonic acid is sodium alkyl benzene sulfonate.

13. The method of claims 4 wherein the water soluble salt is sodium lauryl sulfate.

14. The method of claim 4 wherein the water soluble salt is a sulfated monoglyceride.

15. The method of claims 1, 3 or 4 wherein the matrix is an elastomer.

16. The method of claim 15 wherein the elastomer comprises rubber.

17. The method of claim 16 wherein the matrix is a high melting point wax.

* * * * *